(12) United States Patent
Magaña Castro et al.

(10) Patent No.: US 11,779,574 B2
(45) Date of Patent: Oct. 10, 2023

(54) GEL CONTAINING PIRFENIDONE

(71) Applicant: Excalibur Pharmaceuticals, Inc., New York, NY (US)

(72) Inventors: José Agustín Rogelio Magaña Castro, Mexico City (MX); Laura Vázquez Cervantes, Mexico City (MX); Juan Socorro Armendáriz Borunda, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 3 days.

(21) Appl. No.: 17/390,368

(22) Filed: Jul. 30, 2021

(65) Prior Publication Data

US 2022/0016096 A1    Jan. 20, 2022

Related U.S. Application Data

(60) Continuation of application No. 16/450,150, filed on Jun. 24, 2019, now Pat. No. 11,083,719, which is a division of application No. 15/435,494, filed on Feb. 17, 2017, now Pat. No. 10,376,500, which is a division of application No. 13/893,626, filed on May 14, 2013, now abandoned, which is a division of application No. 12/673,304, filed as application No. PCT/MX2008/000107 on Aug. 14, 2008, now Pat. No. 8,492,412.

(30) Foreign Application Priority Data

Aug. 14, 2007 (MX) .................... MX/a/2007/009796

(51) Int. Cl.

| A61K 31/4418 | (2006.01) |
|---|---|
| A61K 9/00 | (2006.01) |
| A61K 9/06 | (2006.01) |
| A61K 47/02 | (2006.01) |
| A61K 47/18 | (2017.01) |
| A61K 47/22 | (2006.01) |
| A61K 47/32 | (2006.01) |

(52) U.S. Cl.
CPC ........ *A61K 31/4418* (2013.01); *A61K 9/0014* (2013.01); *A61K 9/06* (2013.01); *A61K 47/02* (2013.01); *A61K 47/18* (2013.01); *A61K 47/22* (2013.01); *A61K 47/32* (2013.01)

(58) Field of Classification Search
CPC .... A61K 31/4418; A61K 47/18; A61K 47/22; A61K 9/0014; A61K 9/06
See application file for complete search history.

(56) References Cited

U.S. PATENT DOCUMENTS

| 4,105,782 A | 8/1978 | Yu et al. |
|---|---|---|
| 4,256,877 A | 3/1981 | Karlsson et al. |
| 4,376,118 A | 3/1983 | Daher et al. |
| 5,009,895 A | 4/1991 | Lui |
| 5,310,562 A | 5/1994 | Margolin |
| 5,811,130 A | 9/1998 | Boettner et al. |
| 5,958,420 A | 9/1999 | Jenson |
| 6,365,131 B1 | 4/2002 | Doshi et al. |
| 7,109,246 B1 | 9/2006 | Hawtin |
| 8,492,412 B2 | 7/2013 | Magana Castro et al. |
| 8,603,965 B2 | 12/2013 | Zhou et al. |
| 9,408,836 B2 | 8/2016 | Armendariz Borunda et al. |
| 9,949,959 B2 | 4/2018 | Armendariz Borunda et al. |
| 9,962,374 B2 | 5/2018 | Armendariz Borunda et al. |
| 10,376,500 B2 | 8/2019 | Magana Castro et al. |
| 10,383,862 B2 | 8/2019 | Armendariz Borunda et al. |
| 10,792,258 B2 | 10/2020 | Magana Castro et al. |
| 11,083,719 B2 | 8/2021 | Magana Castro et al. |
| 11,576,905 B2 | 2/2023 | Magana Castro et al. |
| 2003/0103941 A1 | 6/2003 | Crombleholme et al. |
| 2004/0029946 A1 | 2/2004 | Arora et al. |
| 2004/0235946 A1 | 11/2004 | Ott |
| 2005/0059626 A1 | 3/2005 | Van Nest et al. |
| 2005/0267018 A1 | 12/2005 | Blatt et al. |
| 2006/0039931 A1 | 2/2006 | Scheiwe et al. |
| 2006/0051339 A1 | 3/2006 | Sivak |
| 2006/0115503 A1 | 6/2006 | Goyal |
| 2006/0198823 A1 | 9/2006 | Blatt |
| 2007/0054842 A1 | 3/2007 | Blatt et al. |
| 2007/0117841 A1 | 5/2007 | Ozes et al. |
| 2007/0128258 A1 | 6/2007 | Faure et al. |
| 2007/0258946 A1 | 11/2007 | Blatt |
| 2008/0319026 A1 | 12/2008 | Gant et al. |
| 2009/0047246 A1 | 2/2009 | Beigelman et al. |
| 2009/0137354 A1 | 5/2009 | Chaudhuri |

(Continued)

FOREIGN PATENT DOCUMENTS

| CN | 1701793 A | 11/2005 |
|---|---|---|
| CN | 101972225 A | 2/2011 |

(Continued)

OTHER PUBLICATIONS

Suga et al., Exp. Toxic Pathol, 1995;47:287-291 (Year: 1995).*
International Preliminary Report on Patentability dated Jan. 28, 2018 for Application No. PCT/MX2017/000129.
International Search Report and Written Opinion dated Apr. 9, 2018 for Application No. PCT/MX2017/000129.
International Search Report and Written Opinion, PCT/MX2018/000071, dated Mar. 28, 2019, 12 pages.
International Preliminary Report on Patentability, PCT/MX2018/000071, dated Jul. 19, 2019, 7 pages.
International Preliminary Report on Patentability dated Aug. 7, 2013 for Application No. PCT/MX2012/000067.
International Search Report and Written Opinion dated Nov. 22, 2012 for Application No. PCT/MX2012/000067.

(Continued)

*Primary Examiner* — San Ming R Hui
(74) *Attorney, Agent, or Firm* — Wolf, Greenfield & Sacks, P.C.

(57) ABSTRACT

The invention relates to a gel composition containing pirfenidone, which is advantageous over other cutaneously administered pharmaceutical forms known in the prior art and which can be used in treatment for the restoration of tissues with fibrotic lesions and for the prevention of fibrotic lesions.

19 Claims, No Drawings

(56) References Cited

U.S. PATENT DOCUMENTS

| | | |
|---|---|---|
| 2010/0221217 A1 | 9/2010 | Porter et al. |
| 2010/0256031 A1 | 10/2010 | Wu et al. |
| 2011/0034495 A1 | 2/2011 | Seiwert et al. |
| 2011/0224265 A1 | 9/2011 | Magana Castro et al. |
| 2012/0283328 A1 | 11/2012 | Modi |
| 2013/0225639 A1 | 8/2013 | Robinson et al. |
| 2013/0245073 A1 | 9/2013 | Magana Castro et al. |
| 2013/0345165 A1 | 12/2013 | Smith et al. |
| 2014/0296300 A1 | 10/2014 | Armendariz Borunda et al. |
| 2015/0148382 A1 | 5/2015 | Armendariz Borunda et al. |
| 2015/0231098 A1 | 8/2015 | Magana Castro et al. |
| 2016/0228424 A1 | 8/2016 | Armendariz Borunda et al. |
| 2016/0287567 A1 | 10/2016 | Armendariz Borunda et al. |
| 2017/0216268 A1 | 8/2017 | Magana Castro et al. |
| 2018/0066228 A1 | 3/2018 | Smith et al. |
| 2018/0092893 A1 | 4/2018 | Armendariz Borunda et al. |
| 2018/0214434 A1 | 8/2018 | Armendariz Borunda et al. |
| 2018/0353448 A1 | 12/2018 | Magana Castro et al. |
| 2019/0030012 A1 | 1/2019 | Surber |
| 2019/0160048 A1 | 5/2019 | Biber et al. |
| 2019/0262325 A1 | 8/2019 | Armendariz Borunda et al. |
| 2019/0290606 A1 | 9/2019 | Magana Castro et al. |
| 2019/0358213 A1 | 11/2019 | Armendariz Borunda et al. |
| 2020/0016138 A1 | 1/2020 | Magana Castro et al. |
| 2020/0038386 A1 | 2/2020 | Armendariz Borunda et al. |
| 2020/0061040 A1 | 2/2020 | Armendariz Borunda et al. |
| 2020/0253944 A1 | 8/2020 | Magana Castro et al. |
| 2021/0093593 A1 | 4/2021 | Magana Castro et al. |
| 2021/0346360 A1 | 11/2021 | Armendariz Borunda et al. |
| 2021/0386724 A1 | 12/2021 | Armendariz Borunda et al. |
| 2021/0401989 A1 | 12/2021 | Armendariz Borunda et al. |
| 2023/0117397 A1 | 4/2023 | Aguilar-Cordova et al. |

FOREIGN PATENT DOCUMENTS

| | | |
|---|---|---|
| CN | 101972236 A | 2/2011 |
| CN | 102488660 A | 6/2012 |
| CN | 102670600 A | 9/2012 |
| CN | 102670632 A | 9/2012 |
| CN | 103550242 A | 2/2014 |
| EP | 1356816 A1 | 10/2003 |
| EP | 2177220 A1 | 4/2010 |
| EP | 2832354 A1 | 2/2015 |
| EP | 2907506 | 8/2015 |
| JP | 8-510251 A | 10/1996 |
| JP | 2002-506820 A | 3/2002 |
| JP | 2006-503026 A | 1/2006 |
| JP | 2011-506446 A | 3/2011 |
| JP | 2014-505733 A | 3/2014 |
| JP | 2014-522861 A | 9/2014 |
| JP | 2015-513359 A | 5/2015 |
| JP | 2015-526528 A | 9/2015 |
| JP | 2016-515525 A | 5/2016 |
| JP | 2016-517444 A | 6/2016 |
| MX | 2013008151 A | 10/2013 |
| WO | WO 1999/047140 A1 | 9/1999 |
| WO | WO 2000/016775 A1 | 3/2000 |
| WO | WO 2004/073713 A1 | 9/2004 |
| WO | WO 2004/078193 A1 | 9/2004 |
| WO | WO 2004/078194 A1 | 9/2004 |
| WO | WO 2004/078207 A1 | 9/2004 |
| WO | WO 2004/089283 A2 | 10/2004 |
| WO | WO 2005/000227 A1 | 1/2005 |
| WO | WO 2005/037214 A2 | 4/2005 |
| WO | WO 2006/122154 A2 | 11/2006 |
| WO | WO 2007/038315 A2 | 4/2007 |
| WO | WO 2008/107873 A1 | 9/2008 |
| WO | WO 2009/022899 A1 | 2/2009 |
| WO | WO 2013/012307 A1 | 1/2013 |
| WO | WO 2013/147577 A1 | 10/2013 |
| WO | WO 2013/181691 A1 | 12/2013 |
| WO | WO 2014/036487 A1 | 3/2014 |
| WO | WO 2014/055548 A1 | 4/2014 |
| WO | WO 2016/185182 A1 | 11/2016 |
| WO | WO 2017/104725 A1 | 6/2017 |
| WO | WO 2018/088886 A1 | 5/2018 |
| WO | WO 2018/189012 A1 | 10/2018 |
| WO | WO 2019/035705 A2 | 2/2019 |

OTHER PUBLICATIONS

International Preliminary Report on Patentability dated Dec. 1, 2009 for Application No. PCT/MX2008/000107.

International Search Report dated Dec. 9, 2008 for Application No. PCT/MX2008/000107.

International Search Report and Written Opinion dated Jun. 5, 2013 for Application No. PCT/MX2013/000027.

International Preliminary Report on Patentability dated Dec. 19, 2014 for Application No. PCT/MX2013/000099.

International Search Report and Written Opinion dated Aug. 8, 2014 for Application No. PCT/MX2013/000099.

International Search Report and Written Opinion, for Application No. PCT/MX2019/000093, dated Aug. 4, 2020.

International Preliminary Report on Patentability, for Application No. PCT/MX2019/000093, dated Jan. 12, 2021.

International Search Report and Written Opinion, for Application No. PCT/US2021/027335, dated Jul. 12, 2021.

[No Author Listed] Understanding Acne Treatment. Retrieved from https://1www.Webmd.com/skin-problems-and-treatnnents/acne/understanding-acne-treatnnent#5 on Feb. 4, 2019. 5 pages.

[No Author Listed], Allicinnow, "allicin," retrieved online at: http://www.allicinnow.com/allicin/acne-treatmentl, 2 pages (2010).

Armendariz-Borunda et al., A Controlled Clinical Trial With Pirfenidone in the Treatment of Pathological Skin Scarring Caused by Bums in Pediatric Patients, Annals of Plastic Surgery, vol. 68(1):22-28 (2012).

Database WPI Section Ch, Week 200629 Thomson Scientific, London, GB; Class B03, AN 2006-273778, WU, Use of pirfenidone for treating hepatic injury and necrosis and acute lung injury. Shanghai Genomics) p. 7; (2005).

Database WPI Section Ch, Week 201139 Thomson Scientific, London, GB; Class A96, AN 2011-D92901, LI X: Sustained-release tablet comprises pirfenidone, substance capable of releasing active ingredient, and additive, Med Pharm Sci& Technology Co , 1 page (2011).

Database WPI Section Ch, Week 201427 Thomson Scientific, London, GB; Class A96, AN 2014-F77081, Deng C et al., Pharmaceutical composition used for treating hepatic fibrosis, liver fibrosis, liver cirrhosis, and liver cancer comprises pirfenidone, inosine, and auxiliary materials. Sichuan Guokang Pharm Co Ltd, 1 page (2014).

Garcia et al., Pirfenidone effectively reverses experimental liver fibrosis. J Hepatol. Dec. 2002;37(6):797-805.

Josling, Peter Josling's PowerPoint on AllicinCenter Products and Their Uses. retrieved from the internet at: http://allicincenter.com/reference.php?id=products, 15 pages (2013).

Macias-Barragan et al., Methyl-1-Phenyl-2-(IH)-Pyridone Treatment Improves Markers of Hepatic Function and Fibrosis in Steatosis Included By High Fat/Carbohydrate Diet. J Hepatology, Abstract of the International Liver Congress™ 2014—49th Annual Meeting of the European Association for the Study of the Liver, Abstract p. 428, 'ol. 60(1)Suppl.1: S210 (2014).

Macias-Barragan et al., Pirfenidone LP activates PPARalpha and LXRalpha and results in decreased expression of proinflammatory cytokines and improvement of NASH features induced by high fat/carbohydrate diet. Hepatology—Special Issue: The 67th Annual Meeting of the American Association for the Study of Liver Diseases: The Liver Meeting 2016, Abstract No. 1541: vol. 64(SI): 767A-768A: 2 pages (2016).

Nakanishi et al., Pirfenidone inhibits the induction of iNOS stimulated by interleukin-lbeta at a step of NF-kappaE DNA binding in hepatocytes. J Hepatology, vol. 41(5):730-736 (2004).

Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.

(56) References Cited

OTHER PUBLICATIONS

Ozes et al., Preclinical activity of pirfenidone (5-methyl-1phenyl-2 (IH)-pyri done) in cell-based models of nonalcoholic steatohepatitis. Hepatology, Abstract 697, 2003;34(4): 495A.

Park et al., Pirfenidone suppressed the development of glomerulosclerosis in the FGS/Kist mouse. J Korean Med Sci. Aug. 2003;18(4):527-33.

Tiwari et al., Applications of Complementary Polymers in HPMC Hydrophilic Extended Release Matrices. Drug Delivery Technology, Formulating Hydrophilic Matrix Systems, 2009;9(7), 7 pages.

Veras-Castillo et al., Controlled clinical trial with pirfenidone in the treatment of breast capsular contracture:Association ofTGF polymorphisms. Annals Plastic Surgery. 2014;70(1):16-22.

Wang et al., Remdesivir and chloroquine effectively inhibit the recently emerged novel coronavirus (2019-nCoV) in vitro. Cell Res. Mar. 2020;30(3):269-271. doi: 10.1038/s41422-020-0282-0. Epub Feb. 4, 2020. PMID: 32020029; PMCID: PMC7054408.

International Preliminary Report on Patentability dated Oct. 9, 2014 for Application No. PCT/MX2013/000027.

International Preliminary Report on Patentability, dated Oct. 27, 2022 for Application No. PCT/US2021/027335.

[No Author Listed], Efficacy of Pirfenidone Plus MODD in diabetic foot ulcers. NCT02632877. Last updated: Dec. 17, 2015. Retrieved May 17, 2022 from <https://clinicaltrials.gov/ct2/show/NCT02632877?term=NCT02632877>. 8 pages.

[No Author Listed], Mexico's coronavirus death toll is likely 60% higher than confirmed numbers. Reuters. Mar. 29, 2021. Accessed from <https://www.nbcnews.com/news/latino/mexicos-coronavirus-death-toll-likely-60-higher-confirmed-numbers-rcna531> on Jan. 10, 2023. 3 pages.

[No Author Listed], Severe Outcomes Among Patients with Coronavirus Disease 2019 (COVID-19)—United States, Feb. 12-Mar. 16, 2020. CDC COVID-19 Response Team. MMWR Morb Mortal Wkly Rep. Mar. 27, 2020;69(12):343-346. doi: 10.15585/mmwr.mm6912e2.

Azuma et al., Double-blind, placebo-controlled trial of pirfenidone in patients with idiopathic pulmonary fibrosis. Am J Respir Crit Care Med. May 1, 2005;171(9):1040-7. doi: 10.1164/rccm.200404-571OC. Epub Jan. 21, 2005.

Bednarek et al., Skin Antiseptics. In:StatPearls. Jan. 2022. Retrieved from https://www.ncbi.nlm.nih.gov/books/NBK507853 Jun. 9, 2022.

Bhatraju et al., Covid-19 in Critically Ill Patients in the Seattle Region—Case Series. N Engl J Med. May 21, 2020;382(21):2012-2022. doi: 10.1056/NEJMoa2004500. Epub Mar. 30, 2020.

Bruss et al., Pharmacokinetics of orally administered pirfenidone in male and female beagles. J Vet Pharmacol Ther. Oct. 2004;27(5):361-7. doi: 10.1111/j.1365-2885.2004.00612.x.

Cain et al., Inhibition of tumor necrosis factor and subsequent endotoxin shock by pirfenidone. Int J Immunopharmacol. Dec. 1998;20(12):685-95. doi: 10.1016/s0192-0561(98)00042-3.

Choudhuri et al., SARS-CoV-2 PCR cycle threshold at hospital admission associated with patient mortality. PLoS One. Dec. 31, 2020;15(12):e0244777. doi: 10.1371/journal.pone.0244777.

Gancedo et al., Pirfenidone prevents capsular contracture after mammary implantation. Aesthetic Plast Surg. Jan. 2008;32(1):32-40. doi: 10.1007/s00266-007-9051-4.

Gennaro, Remington's Pharmaceutical Sciences. 1990; 18th Ed. pp. 1288-1289, 1291-1292.

Gu et al., Pirfenidone inhibits cryoablation induced local macrophage infiltration along with its associated TGFb1 expression and serum cytokine level in a mouse model. Cryobiology. Jun. 2018;82:106-111. doi: 10.1016/j.cryobiol.2018.03.012. Epub Apr. 3, 2018.

Guo et al., Pirfenidone inhibits epithelial-mesenchymal transition and pulmonary fibrosis in the rat silicosis model. Toxicol Lett. Jan. 2019;300:59-66. doi: 10.1016/j.toxlet.2018.10.019. Epub Oct. 28, 2018.

Huang et al., Clinical features of patients infected with 2019 novel coronavirus in Wuhan, China. Lancet. Feb. 15, 2020;395(10223):497-506. doi: 10.1016/80140-6736(20)30183-5. Epub Jan. 24, 2020. Erratum in: Lancet. Jan. 30, 2020.

Janka-Zires et al., Topical Administration of Pirfenidone Increases Healing of Chronic Diabetic Foot Ulcers: A Randomized Crossover Study. J Diabetes Res. 2016;2016:7340641. doi: 10.1155/2016/7340641. Epub Jul. 10, 2016.

King et al., A phase 3 trial of pirfenidone in patients with idiopathic pulmonary fibrosis. N Engl J Med. May 29, 2014;370(22):2083-92. doi: 10.1056/NEJMoa1402582. Epub May 18, 2014. Erratum in: N Engl J Med. Sep. 18, 2014;371(12):1172.

Moises et al., A Double-blind, Multicenter Study Comparing Pirfenidone and Prednisone for Moderate-to-Severe Pulmonary Fibrosi. Chest J. Jan. 1, 2003;124(4)Suppl:116S. Abstract Only. doi: 10.1378/chest.124.4_MeetingAbstracts.116S-b.

Nagai et al., Open-label compassionate use one year-treatment with pirfenidone to patients with chronic pulmonary fibrosis. Intern Med. Dec. 2002;41(12):1118-23. doi: 10.2169/internalmedicine.41.1118.

Nakazato et al., A novel anti-fibrotic agent pirfenidone suppresses tumor necrosis factor-alpha at the translational level. Eur J Pharmacol. Jun. 20, 2002;446(1-3):177-85. doi: 10.1016/s0014-2999(02)01758-2.

Oku et al., Pirfenidone suppresses tumor necrosis factor-alpha, enhances interleukin-10 and protects mice from endotoxic shock. Eur J Pharmacol. Jun. 20, 2002;446(1-3):167-76. doi: 10.1016/s0014-2999(02)01757-0.

Olivas-Martinez et al., In-hospital mortality from severe COVID-19 in a tertiary care center in Mexico City; causes of death, risk factors and the impact of hospital saturation. PLoS One. Feb. 3, 2021;16(2):e0245772. doi: 10.1371/journal.pone.0245772. Erratum in: PLoS One. May 23, 2022;17(5):e0269053.

Orozco et al., Economic evaluation of topical administration of gel with pirfenidone (Kitoscell Q®) as an adjuvant in the treatment of patients with diabetic foot ulcers. PMD63. Value in Health. May 2017; 20(5):A246.

Raghu et al.,,Treatment of idiopathic pulmonary fibrosis with a new antifibrotic agent, pirfenidone: results of a prospective, open-label Phase II study. Am J Respir Crit Care Med. Apr. 1999;159(4 Pt 1):1061-9. doi: 10.1164/ajrccm.159.4.9805017.

Rao et al., A Systematic Review of the Clinical Utility of Cycle Threshold Values in the Context of COVID-19. Infect Dis Ther. Sep. 2020;9(3):573-586. doi: 10.1007/s40121-020-00324-3. Epub Jul. 28, 2020. Erratum in: Infect Dis Ther. Aug. 18, 2020.

Rubino et al., Effect of food and antacids on the pharmacokinetics of pirfenidone in older healthy adults. Pulm Pharmacol Ther. Aug. 2009;22(4):279-85. doi: 10.1016/j.pupt.2009.03.003. Epub Mar. 27, 2009.

Schaefer et al., Antifibrotic activities of pirfenidone in animal models. Eur Respir Rev. Jun. 2011;20(120):85-97. doi: 10.1183/09059180.00001111.

Selman et al., Idiopathic pulmonary fibrosis: prevailing and evolving hypotheses about its pathogenesis and implications for therapy. Ann Intern Med. Jan. 16, 2001;134(2):136-51. doi: 10.7326/0003-4819-134-2-200101160-00015.

Sun et al., Pharmacokinetic and pharmacometabolomic study of pirfenidone in normal mouse tissues using high mass resolution MALDI-FTICR-mass spectrometry imaging. Histochem Cell Biol. Feb. 2016;145(2):201-11. doi: 10.1007/s00418-015-1382-7. Epub Dec. 8, 2015.

Sun et al., Pharmacometabolic response to pirfenidone in pulmonary fibrosis detected by MALDI-FTICR-MSI. Eur Respir J. Sep. 15, 2018;52(3):1702314. doi: 10.1183/13993003.02314-2017.

Wang et al., Clinical Features of 69 Cases With Coronavirus Disease 2019 in Wuhan, China. Clin Infect Dis. Jul. 28, 2020;71(15):769-777. doi: 10.1093/cid/ciaa272.

Wu et al., Risk Factors Associated With Acute Respiratory Distress Syndrome and Death in Patients With Coronavirus Disease 2019 Pneumonia in Wuhan, China. JAMA Intern Med. Jul. 1, 2020;180(7):934-943. doi: 10.1001/jamainternmed.2020.0994. Erratum in: JAMA Intern Med. Jul. 1, 2020;180(7):1031.

Zhang et al., Pirfenidone reduces fibronectin synthesis by cultured human retinal pigment epithelial cells. Aust N Z J Ophthalmol. May 1998;26 Suppl 1:S74-6. doi: 10.1111/j.1442-9071.1998.tb01380.x.

Zhou et al., Clinical course and risk factors for mortality of adult inpatients with COVID-19 in Wuhan, China: a retrospective cohort study. Lancet. Mar. 28, 2020;395(10229):1054-1062. doi: 10.1016/

(56) References Cited

OTHER PUBLICATIONS

S0140-6736(20)30566-3. Epub Mar. 11, 2020. Erratum in: Lancet. Mar. 28, 2020;395(10229):1038. Erratum in: Lancet. Mar. 28, 2020;395(10229):1038.
Application of addition polymers in hydrophilic hydroxypropyl methylcellulose extended release matrix tablets. Colorcon China, Inc. China Academic Journal Electronic Publishing House. 2022. 3 pages.
Armendáriz-Borunda et al., A pilot study in patients with established advanced liver fibrosis using pirfenidone. Gut. Nov. 2006;55(11):1663-5. doi: 10.1136/gut.2006.107136.
Chen et al., Early detection of nonalcoholic steatohepatitis in patients with nonalcoholic fatty liver disease by using MR elastography. Radiology. Jun. 2011;259(3):749-56. doi: 10.1148/radiol.11101942. Epub Apr. 1, 2011.
Didiasova et al., Pirfenidone exerts antifibrotic effects through inhibition of GLI transcription factors. FASEB J. May 2017;31(5):1916-1928. doi: 10.1096/fj.201600892RR. Epub Feb. 1, 2017.
Gao et al., Pirfenidone Alleviates Choroidal Neovascular Fibrosis through TGF-β/Smad Signaling Pathway. J Ophthalmol. Feb. 1, 2021;2021:8846708. doi: 10.1155/2021/8846708.
Güvenç et al., Pirfenidone Attenue Epidural Fibrosis In Rats By Suppressing TNF-α, IL-1, and α-SMA. J Turk Spin Surg. Jul. 2018;29(3):133-40.
Ishinaga et al., TGF-β induces p65 acetylation to enhance bacteria-induced NF-κB activation. Embo J. Feb. 2, 2007;26(4):1150-62. doi: 10.1038/sj.emboj.7601546. Epub Feb. 1, 2007.
Loomba et al., GS-0976 Reduces Hepatic Steatosis and Fibrosis Markers in Patients With Nonalcoholic Fatty Liver Disease. Gastroenterology. Nov. 2018;155(5):1463-1473.e6. doi: 10.1053/j.gastro. 2018.07.027. Epub Jul. 27, 2018.
Lopez-De La Mora et al., Role and New Insights of Pirfenidone in Fibrotic Diseases. Int J Med Sci. Oct. 14, 2015;12(11):840-7. doi: 10.7150/ijms.11579.
McCommis et al., Treating Hepatic Steatosis and Fibrosis by Modulating Mitochondrial Pyruvate Metabolism. Cell Mol Gastroenterol Hepatol. 2019;7(2):275-284. doi: 10.1016/j.jcmgh.2018.09.017. Epub Oct. 10, 2018.
Pepin, K., Liver Fat Does Not Affect Liver Stiffness Measured with MR Elastography. Resoundant Fact Sheet. 2019. Accessed from < https://www.resoundant.com/single-post/2019/05/21/fact-sheet-liver-fat-does-not-affect-liver-stiffness-measured-with-mr-elastography> on Sep. 21, 2022 2 pages.
Ravishankar et al., A brief review on Pleiotropic effects of Pirfenidone—novel and ongoing outcomes. Int J Res Dev Pharm Life Sci. Jan.-Feb. 2019;8(1):6-14. doi: 10.21276/IJRDPL.2278-0238.2019. 8(1).6-14.
Ruwanpura et al., Pirfenidone: Molecular Mechanisms and Potential Clinical Applications in Lung Disease. Am J Respir Cell Mol Biol. Apr. 2020;62(4):413-422. doi: 10.1165/rcmb.2019- 0328TR.
Selvaraj et al., Diagnostic accuracy of elastography and magnetic resonance imaging in patients with Nafld: A systematic review and meta-analysis. J Hepatol. Oct. 2021;75(4):770- 785. doi: 10.1016/j.jhep.2021.04.044. Epub May 13, 2021.
Wilson et al., Another Weapon in the Battle against Idiopathic Pulmonary Fibrosis? Am J Respir Cell Mol Biol. Apr. 2019;60(4):386-387. doi: 10.1165/rcmb.2018-0387ED.
Wygrecka et al., Pirfenidone exerts anti-fibrotic effects through Inhibition of GLI transcription factors. Pneumologie. Feb. 21, 2018;72(S 01):S114-5. doi: 10.1055/s-0037-1619431.
Zhang et al., Liver fibrosis imaging: A clinical review of ultrasound and magnetic resonance elastography. J Magn Reson Imaging. Jan. 2020;51(1):25-42. doi: 10.1002/jmri.26716. Epub Mar. 12, 2019. Author Manuscript, 32 pages.
Ziol et al., Noninvasive assessment of liver fibrosis by measurement of stiffness in patients with chronic hepatitis C. Hepatology. Jan. 2005;41(1):48-54. doi: 10.1002/hep.20506.

\* cited by examiner

GEL CONTAINING PIRFENIDONE

RELATED APPLICATIONS

This application is a continuation of and claims priority under 35 U.S.C. § 120 to U.S. patent application U.S. Ser. No. 16/450,150, filed Jun. 24, 2019, which is a divisional application of and claims priority under 35 U.S.C. § 120 to U.S. patent application Ser. No. 15/435,494, filed on Feb. 17, 2017, which is a divisional application of and claims priority under 35 U.S.C. § 120 to U.S. patent application Ser. No. 13/893,626, filed on May 14, 2013, which is a divisional application of and claims priority under 35 U.S.C. § 120 to U.S. patent application Ser. No. 12/673,304, filed on Apr. 28, 2010, which is a national stage filing under 35 U.S.C. § 371 of International Application PCT/MX2008/000107, filed on Aug. 14, 2008, which claims priority to Mexican Patent Application Serial No. MX/a/2007/009796, filed on Aug. 14, 2007, each of which is incorporated herein by reference.

FIELD OF INVENTION

The present invention is related to a gel formula that contains Pirfenidone, which offers advantages over other pharmaceutical forms of known cutaneous administration in the state of the technique.

BACKGROUND OF THE INVENTION

The 5-methyl-1-phenyl-2(1H)-pyridone, formula;

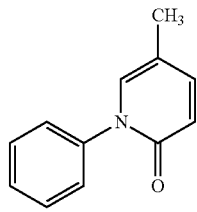

It is a drug that has been applied in the restoration of tissues with lesions with fibrosis and the prevention of fibrotic lesions. This compound, Pirfenidone, it is by itself a known compound and its pharmacological effects has been described, for example, in Japanese applications numbers 87677/1974 and 1284338/1976, as an anti-inflammatory agent that includes antipyretic and analgesics. The U.S. Pat. No. 3,839,346, published Oct. 1, 1974; the number 3, 974, 281, published Aug. 10, 1976; the U.S. Pat. No. 4,042,699 published Aug. 16, 1977, and the U.S. Pat. No. 4,052,509 published Oct. 4, 1977, which described the methods for the obtained Pirfenidone, as well as its use as an anti-inflammatory agent. In the Mexican patent 182, 266 the antifibrotic activity of the 5-methyl-1-phenyl-2(1H)-pyridone is described.

Different resources and treatments have been used to the date and none of them have shown to be really effective. Pirfenidone has shown its efficacy as an anti-fibrotic agent in different pathologies and organs, and has been demonstrated in previous works, where we have observed an effect on the fibroblasts and the production of collagen and extracellular matrix, as well as in experimental models and in clinical tests also.

Many substances could form gels when a gelificant agent is added. This is use in many diverse products in the manufacturing industry, from food to paint, passing through adhesives.

Gels are also important in the chemistry part related with the processes SOL GEL and in the synthesis of solid materials with nanopores.

Gels are classified in: aqueous (hydrogels) or organic (organogels), depending if the aqueous component is water or an organic solvent; organic or inorganic in nature, colloidal or thick grain, according to the size of the particles; and rigid gels, elastic or tixothrophic, according to its mechanic properties.

The hydrocolloids are substances that are produced from vegetable and animal proteins or multiple sugars. They have the capacity to swell themselves and to bind to water. The hydrocolloids are used to thicken, solidify and stabilize food.

OBJECT OF THE INVENTION

The object of the present invention is to provide a gel composition for its cutaneous administration that contains Pirfenidone, a viscous agent; a solubilizer; a non ionic solubilizer; a conserving agent; a neutralizer agent and purified water.

Also, it is the object of the present invention to provide a process of manufacture of a gel that contains pirfenidone for its cutaneous application.

Another objective of the present invention is to provide a gel medicine to be used as an anti-fibrotic and anti-inflammatory agent.

SPECIFICATION OF THE INVENTION

Composition of the Gel

The composition of the gel contains from 2 to 12% of Pirfenidone is elaborated utilizing from 0.4 to 1.2% of a viscous agent, from 10 to 30% of a solubilizer, from 5 to 15% of a non ionic solubilizer, from 0.2 to 1% of a conserving agent, from 0.4 to 1.2% a neutralizer agent and the rest of purify water. The viscous agent is selected from a carbomer 940 (MR); Ultrex 10 (MR), cellulose derivatives; gums; polioxameres; ethylic alcohol and propylenglycol; the conserving agent is selected from a group that consist of Diazolidinyl urea, iodopropinil-butilcarbamate; methylparabene and a mix of these compounds; the neutralizer agent is selected from a group of primary, secondary and tertiary aliphatic amines of the mono-, bi- and triethanolamine type, and of the hydroxide alkaline metals, such as sodium hydroxide.

An example of the composition of the gel is shown in the table 1:

| Component | Quantity (g) | % |
| --- | --- | --- |
| Pirfenidone | 8 | 8 |
| Viscous agent | 0.5 | 0.5 |
| Solubilizer | 20 | 20 |
| Non ionic solubilizer | 11.5 | 11.5 |
| Conserving agent | 0.5 | 0.5 |
| Neutralizer | 0.5 | 0.5 |
| Purified water up to | 100 | 59 |

The gel containing Pirfenidone is manufactured as follows:
 a) Mix 50% of the total water to be used with the viscous agent, allowing the complete humectation of the viscous agent;
 b) Mix separately and with constant agitation the Pirfenidone with the solubilizer agent;

c) Dissolve separately the non ionic solubilizer agent in the 25% water to be used at 40° C., once dissolved, the 15% of the total water is added;
d) Add the solution from part c) to the mix from part b), agitate until the mix is homogenate.
e) Dilute the neutralizer agent 10% of the total water to use, agitate until the mix is homogenate; and
f) Add with constant agitation and homogenate in each addition to the mix from part a) the solution from part d); the conservative and the solution from part e).

A prepared composition according to procedure describe is shown in table 2.

| Component | Quantity (g) |
|---|---|
| Pirfenidone | 8 |
| Carbomer | 0.5 |
| N-methylpirrolidone | 20 |
| Macrogolglycerol Hidroxiestearate 40 | 11.5 |
| Diazolidinilurea and Iodopropinil-butilcarbamate | 0.5 |
| Triethanoalamine | 0.5 |
| Purified water up to | 100 |

These compositions are shown in an example mode, but they are not limited in any level of the reach of the description of the present invention.

The invention claimed is:

1. A method for preparing a composition of pirfenidone gel comprising:
   (i) 2-12% pirfenidone;
   (ii) 0.4-1.2% of a viscous agent selected from the group consisting of Carbomer 940® (crosslinked polyacrylic acid polymer), cellulose derivatives, gums, and poloxamers;
   (iii) 10-30% of a solubilizer selected from the group consisting of N-methylpyrrolidone, ethyl alcohol, and propylene glycol;
   (iv) 5-15% of a non-ionic solubilizer;
   (v) 0.2-1% of a conserving agent selected from the group consisting of diazolidinyl urea, iodopropynyl butylcarbamate, methylparaben, propylparaben, and combinations of these conserving agents;
   (vi) 0.4-1.2% of a neutralizer agent selected from the group consisting of primary, secondary, and tertiary, mono-, bi-, and triethanolamine aliphatic amines, and hydroxide alkaline metals; and
   (vii) water;
the method comprising the steps of:
   (a) mixing approximately 50% of the total water to be used with the viscous agent and allowing complete humectation of the viscous agent;
   (b) mixing pirfenidone and the solubilizer separately and with agitation;
   (c) dissolving separately the non-ionic solubilizer in approximately 25% of total water at approximately 40° C. and once dissolved, adding approximately 15% of the total water;
   (d) adding the solution from part (c) to the mix from part (b), and agitating until homogenous;
   (e) diluting the neutralizer agent in approximately 10% of the total water to be used, and agitating until homogenous; and
   (f) combining the solutions of parts (a)-(e).

2. The method of claim 1, wherein the viscous agent is Carbomer 940®.

3. The method of claim 1, wherein the viscous agent is in the amount of 0.5%.

4. The method of claim 1, wherein the viscous agent is Carbomer 940® and is in the amount of 0.5%.

5. The method of claim 1, wherein the solubilizer is N-methylpyrrolidone.

6. The method of claim 1, wherein the solubilizer is propylene glycol.

7. The method of claim 1, wherein the non-ionic solubilizer is macrogolglycerol hydroxystearate 40.

8. The method of claim 1, wherein the conserving agent is diazolidinyl urea.

9. The method of claim 1, wherein the conserving agent is iodopropynyl butylcarbamate.

10. The method of claim 1, wherein the conserving agent is methylparaben.

11. The method of claim 1, wherein the conserving agent is propylparaben.

12. The method of claim 1, wherein the neutralizer agent is triethanolamine.

13. The method of claim 1, wherein the neutralizer agent is a hydroxide alkaline metal.

14. The method of claim 1, wherein the neutralizer agent is sodium hydroxide.

15. The method of claim 1, wherein the viscous agent is Carbomer 940®, the solubilizer is N-methylpyrrolidone, the conserving agent is diazolidinyl urea, and the neutralizer agent is triethanolamine.

16. The method of claim 1, wherein the viscous agent is Carbomer 940®, the solubilizer is N-methylpyrrolidone, the conserving agent is iodopropynyl butylcarbamate, and the neutralizer agent is triethanolamine.

17. The method of claim 1, wherein the composition of pirfenidone gel comprises: 8% pirfenidone, 0.5% of the viscous agent, 20% of the solubilizer, 11.5% of the non-ionic solubilizer, 0.5% of the conserving agent, 0.5% of the neutralizer agent, and 59% of purified water.

18. The method of claim 1, wherein the viscous agent is Carbomer 940®, the solubilizer is N-methylpyrrolidone, the non-ionic solubilizer is macrogolglycerol hydroxystearate 40, the conserving agent is diazolidinyl urea and iodopropynyl butylcarbamate, and the neutralizer agent is triethanolamine.

19. The method of claim 1, wherein the composition of pirfenidone gel consists of 8% pirfenidone, 0.5% of Carbomer 940®, 20% of N-methylpyrrolidone, 11.5% of the macrogolglycerol hydroxystearate 40, 0.5% of diazolidinyl urea and iodopropynyl butylcarbamate, 0.5% of triethanolamine, and 59% of purified water.

* * * * *